United States Patent
Davis et al.

(10) Patent No.: US 10,625,083 B2
(45) Date of Patent: Apr. 21, 2020

(54) METALLIZED COMPONENTS AND SURGICAL INSTRUMENTS

(71) Applicant: Hutchinson Technology Incorporated, Hutchinson, MN (US)

(72) Inventors: Michael W. Davis, Rockford, MN (US); Douglas P. Riemer, Waconia, MN (US); Clark T. Olsen, Dassel, MN (US); Steven R. Lagergren, Litchfield, MN (US); Paul V. Pesavento, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 95 days.

(21) Appl. No.: 15/630,888

(22) Filed: Jun. 22, 2017

(65) Prior Publication Data
US 2017/0368357 A1    Dec. 28, 2017

Related U.S. Application Data

(60) Provisional application No. 62/355,193, filed on Jun. 27, 2016.

(51) Int. Cl.
*A61B 18/14* (2006.01)
*A61N 1/375* (2006.01)
(Continued)

(52) U.S. Cl.
CPC ............ *A61N 1/375* (2013.01); *B23K 1/0008* (2013.01); *B23K 1/19* (2013.01); *B23K 20/023* (2013.01);
(Continued)

(58) Field of Classification Search
CPC ...... A61B 18/1445; A61N 1/375; B23K 1/19; B23K 20/10
See application file for complete search history.

(56) References Cited

U.S. PATENT DOCUMENTS 4,268,339 A    5/1981    Urban
4,310,823 A    1/1982    Rucker et al.
(Continued)

FOREIGN PATENT DOCUMENTS

EP    1 862 138 A1    12/2007

OTHER PUBLICATIONS

Messler, "Joining of Materials and Structures—From Pragmatic Process to Enabling Technology", Elsevier, 2004, p. 722-741.
(Continued)

*Primary Examiner* — Michael F Peffley
(74) *Attorney, Agent, or Firm* — DLA Piper LLP (US)

(57) ABSTRACT

A surgical instrument and related methods are described. The surgical instrument includes a first jaw including a first structural jaw element and a first sealplate fixed to the first structural jaw element and a second jaw including a second structural jaw element and a second sealplate fixed to the second structural jaw element. The second structural jaw element is moveably coupled to the first structural jaw element to facilitate pinching tissue between the first and second sealplates. The first and second sealplates are configured to facilitate sealing tissue pinched therebetween. The first jaw further includes a metallized tie layer between the first sealplate and the first structural jaw element, wherein the first sealplate is fixed to the first structural jaw element via a metal to metal joint between the first sealplate and the metallized tie layer.

23 Claims, 5 Drawing Sheets

(51) Int. Cl.
| | |
|---|---|
| *C25D 5/48* | (2006.01) |
| *C25D 5/50* | (2006.01) |
| *C25D 7/00* | (2006.01) |
| *C23C 18/16* | (2006.01) |
| *B23K 1/00* | (2006.01) |
| *B23K 1/19* | (2006.01) |
| *B23K 20/02* | (2006.01) |
| *B23K 20/10* | (2006.01) |
| *B23K 20/233* | (2006.01) |
| *C23C 18/32* | (2006.01) |
| *C25D 3/04* | (2006.01) |
| *C25D 5/56* | (2006.01) |
| *C25D 7/06* | (2006.01) |
| *B23K 101/34* | (2006.01) |
| *B23K 103/08* | (2006.01) |
| *B23K 103/00* | (2006.01) |
| *B23K 103/16* | (2006.01) |

(52) U.S. Cl.
CPC ............ *B23K 20/10* (2013.01); *B23K 20/233* (2013.01); *C23C 18/1641* (2013.01); *C23C 18/1689* (2013.01); *C23C 18/1692* (2013.01); *C23C 18/32* (2013.01); *C25D 3/04* (2013.01); *C25D 5/48* (2013.01); *C25D 5/505* (2013.01); *C25D 5/56* (2013.01); *C25D 7/00* (2013.01); *C25D 7/06* (2013.01); *B23K 2101/35* (2018.08); *B23K 2103/08* (2018.08); *B23K 2103/172* (2018.08); *B23K 2103/42* (2018.08); *B23K 2103/52* (2018.08)

(56) References Cited

U.S. PATENT DOCUMENTS

| | | | |
|---|---|---|---|
| 4,594,292 A | 6/1986 | Nagai et al. | |
| 4,837,068 A | 6/1989 | Martin et al. | |
| 5,049,978 A | 9/1991 | Bates et al. | |
| 5,084,124 A | 1/1992 | Taniguchi | |
| 5,151,102 A | 9/1992 | Kamiyama et al. | |
| 5,250,843 A | 10/1993 | Eicheiberger | |
| 5,603,711 A * | 2/1997 | Parins et al. ........... | A61B 17/39 606/51 |
| 5,615,088 A | 3/1997 | Mizumo | |
| 5,637,382 A | 6/1997 | Kataoka et al. | |
| 5,928,547 A | 7/1999 | Shea et al. | |
| 6,140,703 A | 10/2000 | Cronin et al. | |
| 6,251,252 B1 | 6/2001 | Chen | |
| 6,262,436 B1 | 7/2001 | Nakata | |
| 6,333,466 B1 | 12/2001 | Miyaake et al. | |
| 6,334,860 B1 * | 1/2002 | Dorn ....................... | A61B 18/18 606/48 |
| 6,485,999 B1 | 11/2002 | Boone et al. | |
| 6,870,708 B1 | 3/2005 | Fossum et al. | |
| 7,632,565 B1 | 12/2009 | Imam et al. | |
| 8,128,624 B2 | 3/2012 | Couture et al. | |
| 8,623,018 B2 | 1/2014 | Horner et al. | |
| 8,628,557 B2 | 1/2014 | Collings et al. | |
| 8,858,553 B2 | 10/2014 | Chojin | |
| 2001/0035266 A1 | 11/2001 | Kennedy | |
| 2003/0115730 A1 | 6/2003 | Ament et al. | |
| 2006/0049525 A1 | 3/2006 | Lin et al. | |
| 2007/0031741 A1 | 2/2007 | Kim et al. | |
| 2007/0264496 A1 | 11/2007 | Arnold | |
| 2008/0063889 A1 | 3/2008 | Duckham et al. | |
| 2010/0072643 A1 | 3/2010 | Pugh et al. | |
| 2012/0196147 A1 | 8/2012 | Rabiei | |
| 2013/0035685 A1 * | 2/2013 | Fischer ............... | A61B 18/1445 606/41 |
| 2014/0298875 A1 | 10/2014 | Chergui | |
| 2015/0100056 A1 | 4/2015 | Nakamura | |
| 2015/0145379 A1 | 5/2015 | Ito | |
| 2016/0175028 A1 * | 6/2016 | Trees ................... | A61B 18/1445 606/52 |
| 2016/0338719 A1 * | 11/2016 | Allen, IV ............... | A61B 90/03 |
| 2017/0113297 A1 | 4/2017 | Davis et al. | |

OTHER PUBLICATIONS

Raic, Karlo T., et al. "Multilayered Nano-Foils for Low-Temperature Metal-Ceramic Joining." Metalurgija, 14 (2):143-154, 2008.
Schroder, K.A. "Mechanisms of Photonic Curing: Processing High Temperature Films on Low Temperature Substrates." in: Nanotechnology 2011: Electronics, Devices, Fabrication, MEMS, Fluidics and Computational, Chapter 4: NanoFab: Manufacturing & Instrumentation, Nanotech 2011, vol. 2, pp. 220-223.
Schroder, K.A., et al. "Broadcast Photonic Curing of Metallic Nanoparticle Films." NSTI-Nanotech, vol. 3:198-201, 2006.
Wu, Ming-Fang, et al. "Contact Reactive Brazing of Al Alloy/Cu/ Stainless Steel Joints and Dissolution Behaviors of Interlayer." Trans. Nonferrous Met. Soc. China 21:1035-1039, 2011.
International Search Report and Written Opinion in International Application No. PCT/US2016/058902, dated Jan. 3, 2017.
International Search Report and Written Opinion in International Application No. PCT/US2017/039081, dated Sep. 21, 2017.
International Search Report and Written Opinion in International Application No. PCT/US2017/039081, dated Oct. 2, 2017.
Office Action in U.S. Appl. No. 15/334,986, dated Jul. 13, 2017.
Office Action in U.S. Appl. No. 15/334,986, dated Oct. 4, 2017.
International Preliminary Report on Patentability in International Application No. PCT/US2017/039081, dated Jan. 10, 2019.
International Search Report and Written Opinion in International Application No. PCT/US2018/061491, dated Jan. 25, 2019.
International Preliminary Report on Patentability in International Application No. PCT/US2016/058902, dated May 11, 2018.
Office Action in U.S. Appl. No. 15/334,986, dated Jun. 14, 2018.
Office Action in U.S. Appl. No. 15/334,986, dated Jun. 3, 2019.

* cited by examiner

METALLIZED COMPONENTS AND SURGICAL INSTRUMENTS

CROSS-REFERENCE TO RELATED APPLICATIONS

This application claims priority from U.S. Provisional Patent Application No. 62/355,193, filed on Jun. 27, 2016, which is hereby incorporated by reference in its entirety.

This disclosure is related to U.S. patent application Ser. No. 15/334,986, titled, "METALLIZING POLYMERS, CERAMICS AND COMPOSITES FOR ATTACHMENT STRUCTURES," filed Oct. 26, 2016, which claims the benefit of U.S. Provisional Patent Application No. 62/312,012, filed on Mar. 23, 2016, and U.S. Provisional Pat. App. No. 62/246,909, titled, "METALLIZING POLYMERS FOR ATTACHMENT STRUCTURES," filed Oct. 27, 2015. The entire contents of all of these applications are incorporated by reference herein for all purposes.

TECHNICAL FIELD

This disclosure relates generally to techniques for joining polymeric, ceramic, or ceramic-polymer composite components to another component.

BACKGROUND

In overmolding to create structural attachment between a polymeric, ceramic, or ceramic-polymer composite component and underlying component(s) within an assembly, it may be difficult to obtain an adequate bond. This is exacerbated when the overall assembly size is preferably as small as possible, since the overmold requires adding to the volume of the assembly. Overmolded component surfaces may have limited or no adhesion to the surfaces of the underlying component. This lack of adhesion between mating surfaces of an assembly including an overmolded component may limit the strength of the assembly compared to alternatives in which adjacent surfaces of components within an assembly are adhered to each other.

SUMMARY

A surgical instrument and related methods are described. The surgical instrument includes a first jaw including a first structural jaw element and a first sealplate fixed to the first structural jaw element and a second jaw including a second structural jaw element and a second sealplate fixed to the second structural jaw element. The second structural jaw element is moveably coupled to the first structural jaw element to facilitate pinching tissue between the first and second sealplates. The first and second sealplates are configured to facilitate sealing tissue pinched therebetween. The first jaw further includes a metallized tie layer between the first sealplate and the first structural jaw element, wherein the first sealplate is fixed to the first structural jaw element via a metal to metal joint between the first sealplate and the metallized tie layer.

Other features and advantages of embodiments of the present invention will be apparent from the accompanying drawings and from the detailed description that follows.

BRIEF DESCRIPTION OF THE DRAWINGS

Embodiments of the present invention are illustrated by way of example and not limitation in the figures of the accompanying drawings, in which like references indicate similar elements and in which.

DETAILED DESCRIPTION

Manufacture techniques disclosed herein facilitate attachment surfaces on a nonmetallic component, such as a polymeric (e.g., plastic), ceramic, ceramic-polymer composite or glass component for attaching the nonmetallic component to a metal component, or another nonmetallic component. As one example, surfaces to be joined are metallized to provide a 'tie' layer so that alternative bonding methods can be used. For polymeric and ceramic components, the metallized layers can be created with sputtering, such as sputtering with chromium and or copper. For metal components, sputtering or plating, such as nickel plating, can be used if needed to provide a metallized 'tie' layer suitable for joining. The metallized 'tie' layers can be joined with a variety of methods, including, for example, soldering, brazing, adhesive bonding (using an adhesive designed for metal to metal bonding), compression fusion welding, metal fusion bonding, such as gold fusion bonding, and other metal to metal joining techniques. The techniques disclosed herein may be particularly useful for joining plastic to plastic, ceramic to ceramic, ceramic to metal, ceramic to plastic and/or plastic to metal components for products exposed to harsh environments, such as medical applications.

Figure 1A:
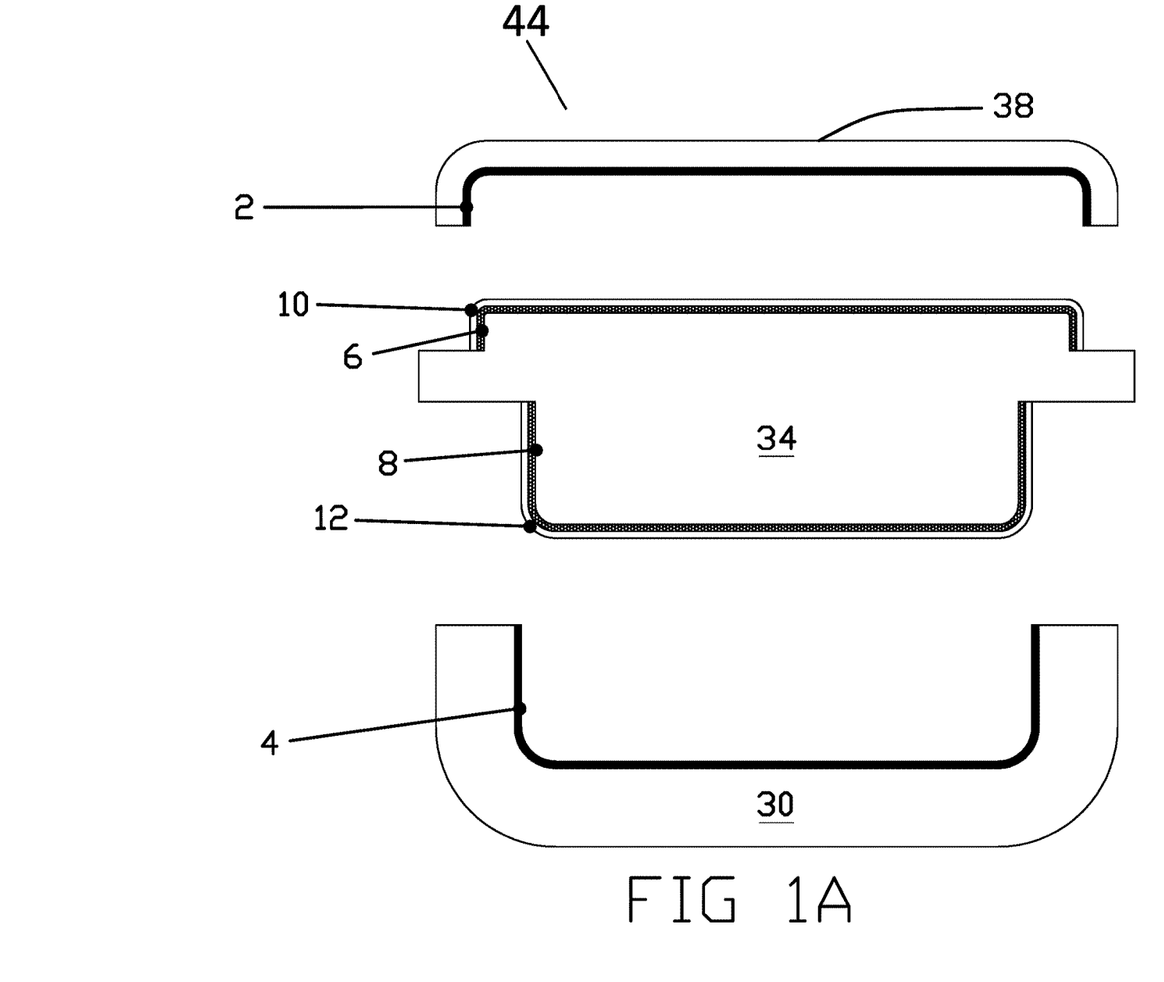
FIGS. 1A and 1B illustrate components of an assembly according to an embodiment.
Figure 1B:
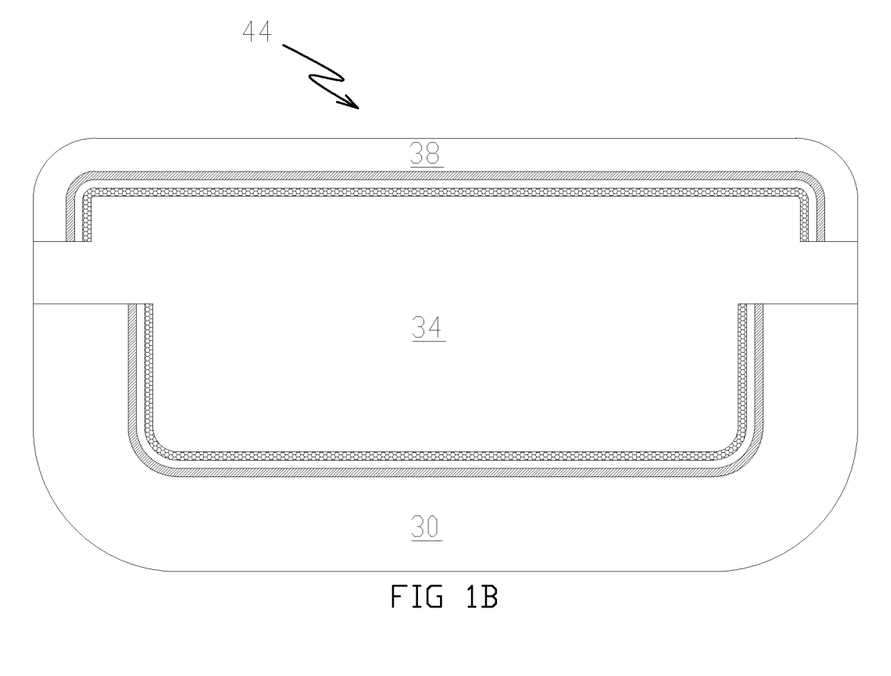

When joining surfaces of components with at least one polymeric or ceramic surface, such as nonmetallic spacer 34 of assembly 44 as illustrated in FIGS. 1A and 1B, bonding directly to the polymeric or ceramic surface may result in poor adhesion. As disclosed herein, first applying a metallized tie layer to the polymeric or ceramic surface provides a different functional surface for an adhesive to bond to. In the case of bonding two polymeric or ceramic components together, both components may be selectively sputtered with a metallized tie layer so that a metal-to-metal adhesive may be applied to join the surfaces. Such metal-to-metal adhesive may provide good bonding to the metallized tie layers and provide improved adhesion as compared to conventional techniques for polymer to polymer, ceramic to ceramic, ceramic to plastic, ceramic to metal and/or plastic to metal bonding.

These techniques may facilitate attaching a formed (planer or non-planar) metal component to a nonmetallic component, such as a support structure, spacer or stand-off, although it could also be used to bond two nonmetallic components. The nonmetallic component can alternatively be formed using other known methods for example, stamping, laser cutting, machining, and extruding.

In the example of two nonmetallic components, the described surface preparation techniques may be applied to both of the nonmetallic surfaces being attached and bonded. For plastic to plastic, ceramic to ceramic or ceramic to plastic surface joining, metalized surfaces may be formed on both nonmetallic components to act as a different surface onto which the bond can occur. Bonding may occur by solder, brazing, Au bonding, adhesives, or other metal to metal bonding techniques.

Certain ceramics, ceramic-polymer composites and plastic resins in the polyamide family such as Zytel, Akromid, Amodel, and similar are difficult to bond to metals including bonding with adhesives. Difficulties in such bonding may occur when the surface is non-planer or has 3D curved surfaces that mate. The techniques disclosed herein may be particularly useful for bonding such ceramics, ceramic-polymer composites and plastic resins to metal, ceramic or polymeric components.

These techniques may be used to create medical, e.g., surgical, instruments, such as electrosurgical or ultrasonic instruments for sealing tissue. Due to improved surface adhesion of adjacent components, surgical instruments assembled using these techniques may be smaller and/or more robust than surgical instruments instead assembled using overmolding techniques.

FIGS. 1A-1B illustrate components of an assembly 44. FIGS. 1A-1B illustrate an assembly technique utilizing solder as the attachment method between the tie layers. In particular, FIG. 1A illustrates an exploded view of the components of assembly 44, whereas FIG. 1B illustrates a cross-sectional view of the attached components of assembly 44.

Assembly 44 includes metal component 30, nonmetallic spacer 34 and stainless steel component 38. As shown in FIG. 1B, metal component 30 and stainless steel component 38 include optional nickel plating layers 2, 4 on a surface to be joined with a nonmetallic spacer 34. Likewise, nonmetallic spacer 34 includes metalized tie layers 6, 8 such as a chromium, copper, and/or nickel layer, as well as solder layers 10, 12 that can be pre-tinned or applied using other known methods, on the surfaces to be joined with metal component 30 and stainless steel component 38. For example, the metallized tie layers 10, 12 may be formed using electroplating, electroless plating, vacuum, deposition, sputtering of metal, and other techniques. Such solder layers 10, 12 may be a solder suitable for use on medical devices, such as Indalloy 121 (or similar). In alternative examples, in which adhesive joining the metallized surfaces is chosen in place of solder, then the solder layer 10, 12 is not needed. Stainless steel component 38 may include a plating layer 4, such as a nickel plating layer.

In some particular examples, assembly 44 may represent components within a medical instrument. In such examples, it may be important to electrically and/or thermally isolate stainless steel component 38 from metal component 30. For example, assembly 44 may represent a jaw member of a surgical instrument for sealing tissue, such as vessel sealing, including, but not limited to, electrothermal sealing and ultrasonic sealing. In such an example, stainless steel component 38 may represent an electrically and/or thermally conductive sealing member referred to as "a sealing plate" that may be heated or electrically charged to facilitate tissue sealing. In some such examples, the thickness of stainless steel component 38 may be about 0.010 inches. In the same or different examples, the thickness of metal component 30 may be about 0.025 inches. Electrically charging stainless steel component 38 may occur using high-frequency electrical signals, such as bipolar electrical signals. Thermally heating stainless steel component 38 may occur using ultrasonic signals, e.g., with a piezoelectric crystal (not shown) adjacent to stainless steel component 38.

Nonmetallic spacer 34 may function to electrically and/or thermally isolate stainless steel component 38 from metal component 30. Metal component 30 may represent a structural component of the jaw member configured to pivot and/or actuate in conjunction with another jaw component to facilitate gripping and manipulation of tissue. The other jaw component may likewise include an electrically conductive sealing member that combines with stainless steel component 38 to facilitate tissue sealing between the two jaw components.

Prior to metal-to-metal bonding techniques to bond metal component 30, nonmetallic spacer 34 and stainless steel component 38 together, the components should be properly aligned as desired for the final assembly. For solder attach bonding, the components may be stacked and aligned and baked to allow the pre-tinned low temp solder to reflow and wet to the metallized portions of the mating pieces. Generally, the solder should wet only to the metallized regions.

In glue attach bonding, (metallized to metallized), adhesive may be applied before stacking and aligning the components. The metallized faces provide an alternative to bonding directly to nonmetallic spacer 34 and may provide stronger adhesion that directly applying an adhesive to nonmetallic spacer 34.

As shown in FIG. 1B, metal component 30, nonmetallic spacer 34 and stainless steel component 38 may be joined by way metal-to-metal bonding techniques, such as solder or other techniques. In this manner, an overmold layer is not needed. The interface surfaces for a strong mechanical attachment provided by the metalized tie layer on nonmetallic spacer 34 allows nonmetallic spacer 34 to be joined using metal joining techniques to other components, such as metal component 30 and stainless steel component 38. These techniques eliminate the need for an overmold.

Assembly 44 provides sealing between metal component 30, nonmetallic spacer 34 and stainless steel component 38. For this reason, in a bending type loading applied to assembly 44, the three layers, i.e., metal component 30, nonmetallic spacer 34 and stainless steel component 38, reinforce each other to provide additional bending strength than with what may be achieved with conventional overmolding.

In some particular examples, assembly 44 may represent components within a medical instrument. In such examples, it may be important to electrically and/or thermally isolate stainless steel component 38 from metal component 30. In some such examples, the thickness of stainless steel component 38 may be about 0.010 inches. In the same or different examples, the thickness of metal component 30 may be about 0.025 inches. Attachment surfaces of metal component 30 and stainless steel component 38 may be optionally nickel plated, chrome plated or plated with other materials to provide the proper tie layer interface. In addition, adjacent surfaces of nonmetallic spacer 34 may be metalized with a tie layer to facilitate bonding to metal component 30 and stainless steel component 38 using metal-to-metal joining techniques. Such metalized tie layers 6, 8 are optionally patterned. In some examples, nonmetallic spacer 34 may be a polymeric component, such as an injection molded fiber filled component, such as glass fiber or carbon fiber component, a ceramic component, or a blend of polymer and ceramic materials forming a composite component.

In a variation of assembly 44, a high strength nonmetallic may be added instead of or in addition to metal component 30 in order to provide structural strength to the assembly. In another variation, the function of metal component 30 and nonmetallic spacer 34 may be replaced by a single high strength nonmetallic component layer.

In a further variation of assembly 44, stainless steel component 38 may be replaced with an electroplated component on nonmetallic spacer 34 or directly on a high strength nonmetallic component layer. Such electroplating and/or electroforming may occur on a metalized tie layer of the nonmetallic component.

Following the formation of a metalized tie layer on the nonmetallic component, the surface of the nonmetallic component may be positioned to mate with a metallic surface of a second component. Then the metallized tie layer on the nonmetallic component may be joined with the mated metallic surface of the second component using metal to metal joining techniques.

The second component may be a metal component or a nonmetallic component with a second metallized tie layer on the second component. In different examples, metallized tie layers may be used for joining plastic to plastic, ceramic to ceramic, ceramic to metal, ceramic to plastic and/or plastic to metal components for products exposed to harsh environments, such as medical applications.

In accordance with the techniques disclosed herein, possible methods of metal-to-metal attachment of one or more nonmetallic components include, fusion of metal (welding), brazing, soldering, adhesive bonding, fusion of plated metals (e.g., via ultrasonics or resistance), or other metal-to-metal bonding techniques as discussed in further detail below.

As the properties of certain base materials, such as metallic components and non-metallic components may be affected at temperatures required for particular bonding techniques, metal-to-metal bonding techniques that do not require temperatures adverse to the base materials may be used. Generally speaking, bonding techniques rely on materially-compatible (wettable and having an ability to form a strong bond after wetting and cooling/solidification), pre-prepared substrate and bonding part surfaces that can readily adhere/bond to the molten metal bonding material.

In addition to the techniques listed above, low temperature melting nanoparticle material bonding techniques may be useful in some examples for joining plastic to plastic, ceramic to ceramic, ceramic to metal, ceramic to plastic and/or plastic to metal components. With low temperature melting nanoparticle material 1 bonding, a "nanoparticle" solder is used that achieves lower processing temperatures by using small particle sizes to fully melt the solder at temperatures the base material of component can handle.

As another example, low temperature and pressure sintering bonding techniques may be useful in some examples for joining plastic to plastic, ceramic to ceramic, ceramic to metal, ceramic to plastic and/or plastic to metal components. With low temperature and pressure sintering bonding, sintering mostly relies on partially melting a bonding material (such as softening/melting the surface of the particles to be sintered) and then applying pressure to form the high surface area strong bond with the components. Such techniques may use a low-temperature "nanoparticle" solder or other sintering materials.

As other examples, melting or reactive photonic curing or sintering bonding may be useful in some examples for joining plastic to plastic, ceramic to ceramic, ceramic to metal, ceramic to plastic and/or plastic to metal components. With melting or reactive photonic curing or sintering bonding, a "flashlamp melted" material may allow for maintaining low temperatures through ultra-fast heating and melting of the bonding material. The bonding material may absorb the flashlamp energy and simply melt or the bonding material may start an exothermic, self-sustaining reaction at the surface which may propagate across and through the film such that the film melts itself and wets and heats the surface of components to form a bond.

As other examples, low temperature and pressure reactive soldering/brazing material bonding may be useful in some examples for joining plastic to plastic, ceramic to ceramic, ceramic to metal, ceramic to plastic and/or plastic to metal components. With low temperature and pressure reactive soldering/brazing material bonding a molten compound formation, typically a eutectic compound, may be located between the metal bonding material and the substrate and component. Such techniques are distinct from those that rely upon a melting of only the bonding material which then wets to the components. The molten material for low temperature and pressure reactive soldering/brazing material bonding can be formed through the application of heat and pressure to get interdiffusion and start the eutectic compound formation, which then melts at the current temp. Alternatively or additionally, the molten material for low temperature and pressure reactive soldering/brazing material bonding can be formed by using multiple-component (mixtures of particles or multilayer films) bonding materials such that they melt and intermix due to an ignition event (such as an electric arc or laser heating at one tiny spot), then, due to high energy of mixing and self-propagating reaction, the entire bonding material melts and gives off enormous amounts of heat, which causes strong bond formation to the substrate and bonding part while maintaining low average/equilibrium temperature and minimizing the thermal effect on substrates.

Alternatives to non-conductive spacer concepts include:
Use of high performance board as the non-conductive spacer. (Such as but not limited to Rogers LoPro RO4000 series high frequency laminates, available from Rogers Corporation of Rogers, Conn., United States). This could be utilized as a laminate (IE—pre clad with conductive layers), and/or it could be an unclad core which is subsequently metallized by techniques discussed above.
Use of powder coating as the non-conductive spacer.

EXAMPLES

Various embodiments of processing options for joining a nonmetallic surface to a metal surface, such as a joining of a nonmetallic surface to a non-planar (3D) metal surface, as shown in FIG. 1B, are described below. These examples are merely representative of the techniques disclosed herein and other techniques may be used within the spirit of this disclosure. Other non-planar metal surfaces that may be used include, but are not limited to, cylindrical or tubular structures such as, but not limited to, joining a metallic tube, rod, or wire to a non-metallic polymer tube.

Example 1

A nonmetallic component, such as a plastic, ceramic or plastic ceramic composite 3D component, is modified with an oxygen containing plasma using techniques including those known in the art. More specifically, a surface of a nonmetallic component may be modified using a plasma source containing oxygen, or argon or both prior to forming a metallized tie layer on the surface of the nonmetallic component. For another embodiment, a surface of a nonmetallic component is modified with an oxygen using an ion source containing oxygen, or argon or both prior to forming a metallized tie layer on the surface of the nonmetallic component. A surface of the nonmetallic component is then sputtered with chromium (Cr) to form a metalized tie layer to a subsequent solderable metal. For other embodiments, a metalized tie layer is formed by sputtering a metal including, but not limited to, titanium (Ti), tantalum (Ta), ruthenium (Ru), nickel-chrome (NiChrome), and nickel-vanadium (NiV). According to some embodiments, the metalized tie layer is deposited using a shadow mask. Yet other embodiments include using a vapor deposition to form a metalized tie layer. For various embodiments, the tie layer is from 50 angstrom to 500 angstroms thick. The tie layer is preferably 75 to 150 angstroms thick. The sputtered subsequent solderable metal is chosen from copper (Cu), nickel (Ni), gold (Au), platinum (Pt), palladium (Pd), silver (Ag), ruthenium (Ru), cadmium (Cd), Tin (Sn), radium (Ra), brass, etc. Other solderable metals may include one that forms an intermetallic without fully dissolving into a solder. Yet another solderable metal that could be used according to embodiments includes one that can be electroplated to a metallic surface of a component. The thickness of the solderable metal, according to some embodiments, may be greater than 500 angstroms and less than 50000 angstroms, such as greater than 1000 angstroms and less than 5000 angstroms.

Example 2

In this example, the techniques of Example 1 are repeated with the addition of compression bonding using gold as the bonding material and chrome as the tie layer.

Example 3

In this example, the techniques of Example 1 are repeated with mismatched metals such as nickel on one surface, Pd on another, or Au on one and nickel on the other, etc.

Example 4

In this example, the techniques of Example 1 are repeated using a nonmetallic component that is difficult to bond using adhesives such as polyamides, polytetraflourides, polydiflourides, etc.

Example 5

In this example, bonding two nonmetallic components are bonded together. Mating surfaces of both components are selectively sputtered with a metallized tie layer so that a metal-to-metal joining techniques, such as a metal-to-metal adhesive may be applied to join the surfaces. Such metal-to-metal adhesive may provide good bonding to the metallized tie layers and provide improved adhesion as compared to conventional techniques for plastic to plastic, ceramic to ceramic or ceramic to plastic bonding.

Figure 2:
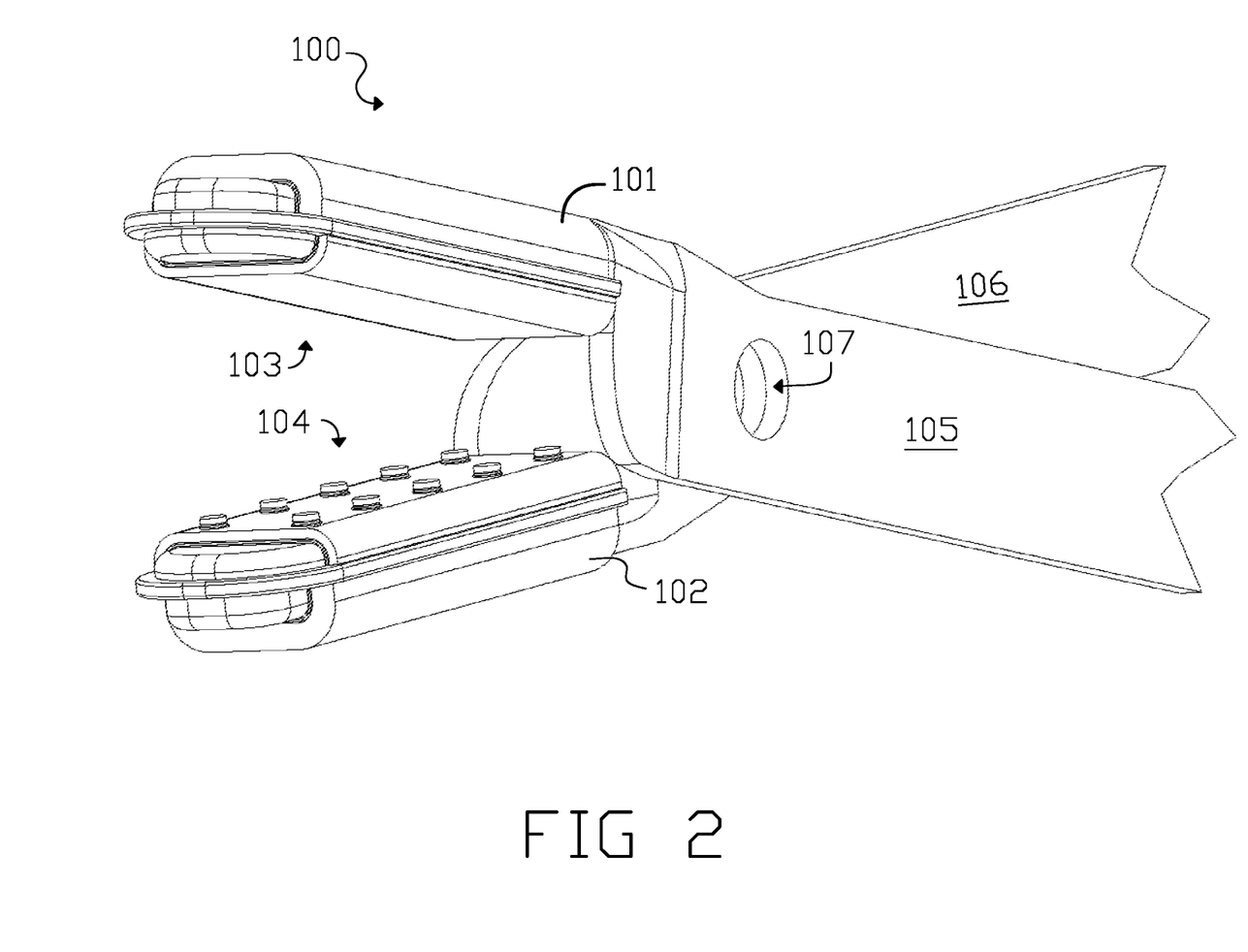
FIG. 2 illustrates a surgical instrument according to an embodiment.

FIG. 2 illustrates a surgical instrument 100 configured to facilitate tissue sealing between sealing surfaces 103, 104 of mating jaw members 101, 102. Mating jaw members 101, 102 include arms 105, 106, which are rotatable relative to one another via pivot joint 107 to allow mating jaw members 101, 102 to open and close. According to the illustrated example, when mating jaw members 101, 102 are closed sealing surfaces 103, 104 are about parallel to one another. In other examples, arms 105, 106, may be rotatable relative to one another to allow mating jaw members 101, 102 to open and close via a different mechanical configuration, such as, for example, a four-bar linkage.

Jaw members 101, 102 may each be manufactured according to the techniques disclosed above with respect to FIGS. 1A and 1B. According to various examples, surgical instrument 100 may be an electrosurgical instrument or an ultrasonic surgical component. In either example, the electrical or ultrasonic activation of sealplates 101, 102 heats sealplates 101, 102 to facilitate tissue sealing for tissues, such as vasculatures or other vessels, pinched between sealing surfaces 103, 104.

Figure 3A:
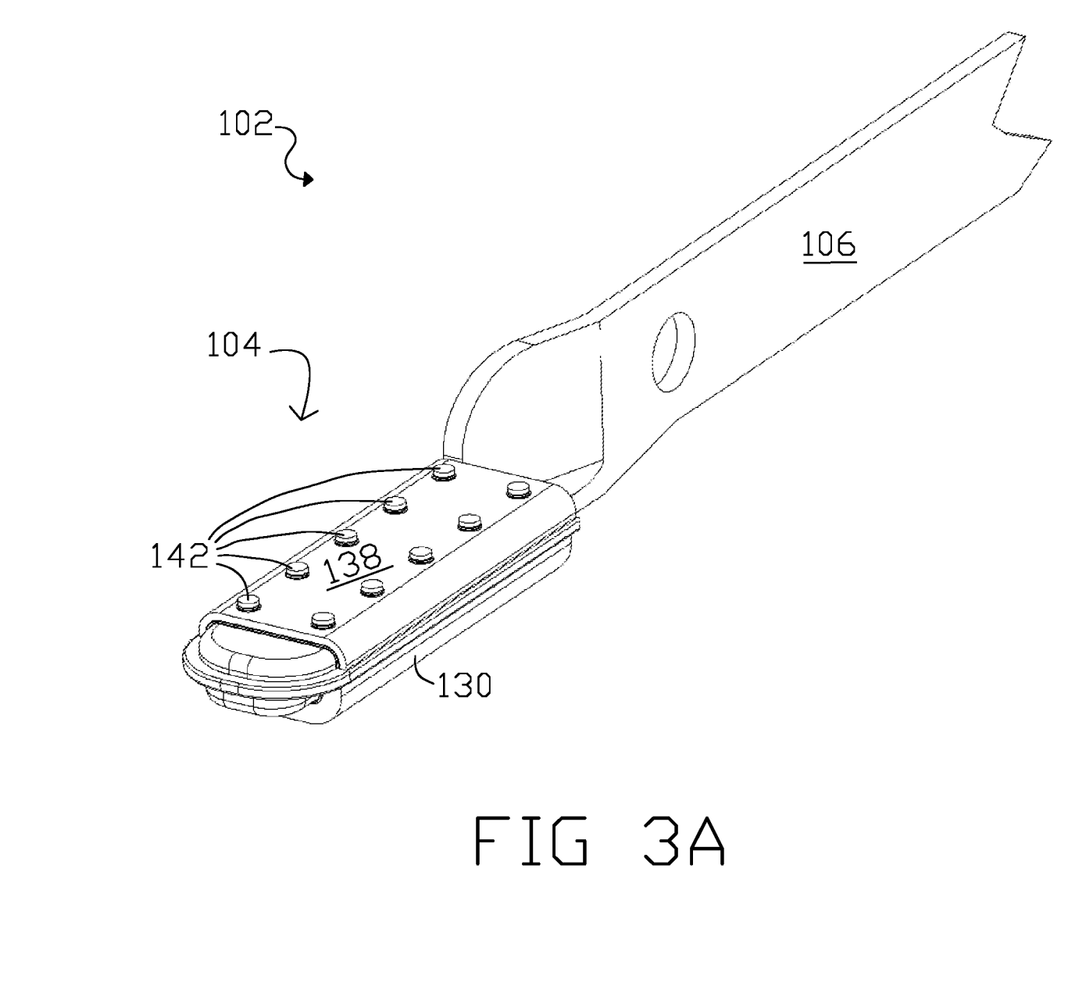
FIGS. 3A and 3B illustrate views of a jaw member of a surgical instrument according to an embodiment.
Figure 3B:
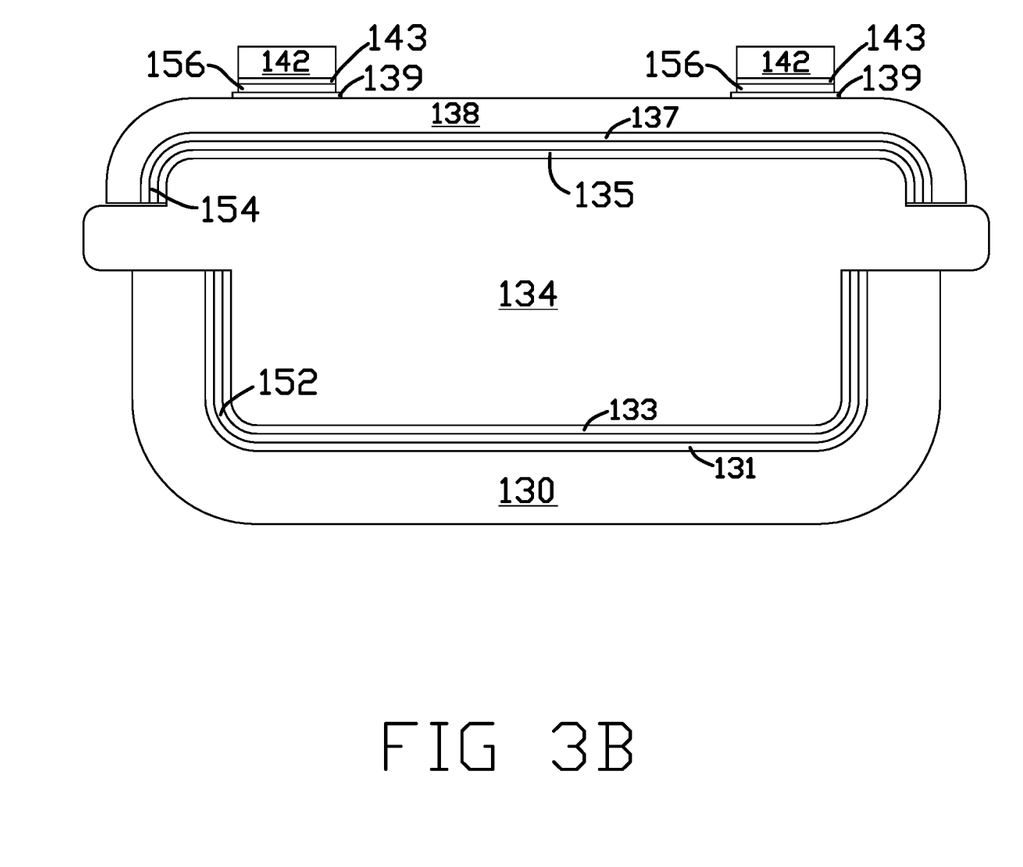

FIGS. 3A and 3B illustrate jaw member 102 in further detail according to some embodiments. In particular, FIG. 3A is a perspective view of jaw member 102, and FIG. 3B is a cross-sectional view of a portion of jaw member 102 including sealing surface 104. Jaw member 102 includes metal component 130, which represents a structural component of jaw member 102. Jaw member 102 also includes sealplate 138, which is heatable to facilitate tissue sealing with the corresponding sealplate of jaw member 101.

Nonmetallic spacer 134 is located between metal component 130 and sealplate 138. Nonmetallic spacer 134 functions to electrically and/or thermally isolate sealplate 138 from metal component 130. In different examples, nonmetallic spacer 134 may be a polymeric component, a ceramic component, a ceramic-polymer composite component, a resin plastic injection molded component, or another nonmetallic component.

Metal component 130 is configured to pivot and/or actuate in conjunction with the corresponding metal component of jaw member 103 to facilitate gripping and manipulation of tissue. In addition to gripping and manipulation of tissue with jaw members 102, 103, the electrical or ultrasonic activation of sealplates 101, 102 heats sealplates 101, 102 to facilitate tissue sealing for tissues, such as vasculatures or other vessels, pinched between sealing surfaces 103, 104.

In some examples, sealplates 101, 102 may be formed from stainless steel. The sealplates, according to various embodiments, may have a thickness in a range of about 0.0001 inches to about 0.02 inches. According to other embodiments, the thicknesses of sealplates 101, 102 may be about 0.010 inches. In the same or different examples, the thickness of metal component 130 may be about 0.025 inches. Electrically charging sealplates 101, 102 may occur using high-frequency electrical signals. Thermally heating sealplates 101, 102 may occur using ultrasonic signals, for example, with a piezoelectric crystal, adjacent to sealplates 101, 102.

Sealplate 102 includes sealplate spacers 142 on sealing surface 104. Sealplate spacers 142 are electrically and/or thermally insulating and function to provide a minimum predefined gap between sealing surfaces 103, 104 when mating jaw members 101, 102 are closed. The predefined gap, defined according to the thicknesses of sealplate spacers 142, may be selected to provide suitable tissue sealing. The gap between sealing surfaces 103, 104 can also prevent undesirable contact between sealing surfaces 103, 104. For example, contact between sealing surfaces 103, 104 may result in the welding of sealplates 101, 102 to one another, especially in examples in which sealplates 101, 102 are electrically activated. Sealplate spacers 142 may further serve to provide texture to sealing surfaces 103, 104, thereby increasing friction between sealing surfaces 103, 104 and tissue pinched between sealing surfaces 103, 104. The material of sealplate spacers 142 should be selected to withstand operating temperatures of sealplates 101, 102. In various examples, sealplate spacers 142 may be polymeric components, ceramic components, ceramic-polymer composite components, a resin plastic injection molded component, undoped silicon components, alumina-filled epoxy components and/or another nonmetallic component. For example, sealplate spacers 142 may be formed from undoped silicon wafers, e.g., via dicing or kiss-cutting.

Sealplate spacers 142 may have thicknesses in the range of about 0.001 inches to about 0.02 inches.

Components of surgical instrument 100 include metallized tie layers 131, 133, 135. 137, 139, 143 to facilitate bonding to adjacent components using metal to metal bonding techniques for metal to metal joints 152, 154, 156. Metal to metal joints 152, 154, 156 may be created with a variety of methods, including, for example, soldering, brazing, adhesive bonding (using an adhesive designed for metal to metal bonding), compression fusion welding, metal fusion bonding, such as gold fusion bonding, and other metal to metal joining techniques. For an example using compression fusion welding, a surface of a nonmetallic component and a surface of a metallic surface are gold plated and the compression fusion weld is made by contacting the two gold plated surfaces and applying an energy source. Examples of an energy source include, but are not limited to, ultrasonic, megasonic, or other types of energy sources.

Metal component 130 includes metallized tie layer 131, which is bonded to metallized tie layer 133 of nonmetallic spacer 134 via metal to metal joint 152. Nonmetallic spacer 134 further includes metallized tie layer 135, which is bonded to optional metallized tie layer 137 of sealplate 138 via metal to metal joint 154. For example, optional metallized tie layer 137 of sealplate 138 may be sputtered or plated on the base metal of sealplate 138. In other examples, metallized tie layer 135 may be bonded directly to the base metal of sealplate 138 via metal to metal joint 154. Sealplate 138 further includes optional metallized tie layer 139, which is bonded to metallized tie layers 143 of sealplate spacers 142 via metal to metal joints 156. Optional metallized tie layer 139 may represent a continuous layer adjacent to more than one of sealplate spacers 142, such as all of sealplate spacers 142 or separate areas, each associated with an individual one of sealplate spacers 142. In other examples, metallized tie layers 143 of sealplate spacers 142 may be bonded directly to the base metal of sealplate 138 via metal to metal joints 156.

When joining surfaces of components with at least one polymeric or ceramic surface, such as nonmetallic spacer 34 of assembly 44 as illustrated in FIG. 1B, bonding directly to the polymeric or ceramic surface may result in poor adhesion. As disclosed herein, first applying a metallized tie layer to the polymeric or ceramic surface provides a different functional surface for an adhesive to bond to. In the case of bonding two polymeric or ceramic components together, both components may be selectively sputtered with a metallized tie layer so that a metal-to-metal adhesive may be applied to join the surfaces. Such metal-to-metal adhesive may provide good bonding to the metallized tie layers and provide improved adhesion as compared to conventional techniques for polymer to polymer, ceramic to ceramic, ceramic to plastic, ceramic to metal and/or plastic to metal bonding.

While jaw member 102 is described as including metal to metal joints 152, 154, 156, in some examples, jaw member 102 may include more or less metal to metal joints. For example, sealplate spacers 142 may be secured to sealplate 138 via metal to metal joints 156, while nonmetallic spacer 134 is an overmolded component without one or both of a metal to metal joints 152, 154.

While only jaw member 102 is described in detail, jaw member 101 is substantially similar to jaw member 102, except for the addition of nonmetallic sealplate spacers 142 on sealing surface 104 of sealplate 138 of jaw member 102. The exception is that jaw member 102 includes nonmetallic sealplate spacers 142 on the sealing surface 104 of sealplate 138. While according to the illustrated example, contrast jaw member 101 does not include nonmetallic sealplate spacers, in other examples, both of sealing surfaces 103, 104 may include nonmetallic sealplate spacers. Such nonmetallic sealplate spacers on both of sealing surfaces 103, 104 may be arranged such that some or all of opposing sealplate spacers on both of sealing surfaces 103, 104 to contact on another or staggered to avoid contact one another.

Although the disclosed techniques have been described with reference to various examples, those skilled in the art will recognize that changes can be made in form and detail without departing from the spirit and scope of this disclosure.

What is claimed is:

1. A surgical instrument comprising:
    a first jaw including a first structural jaw element, a first sealplate fixed to the first structural jaw element, and a first nonmetallic sealplate spacer separating and electrically insulating the first structural jaw element and the first sealplate;
    a second jaw including a second structural jaw element, a second sealplate fixed to the second structural jaw element, and a second nonmetallic sealplate spacer separating and electrically insulating the second structural jaw element and the second sealplate,
    wherein the second structural jaw element is moveably coupled to the first structural jaw element to facilitate pinching tissue between the first and second sealplates, and wherein the first and second sealplates are configured to facilitate sealing tissue pinched therebetween,
    wherein the first jaw further includes a metallized tie layer between the first sealplate and the first nonmetallic sealplate spacer, wherein the first sealplate is fixed to the first nonmetallic sealplate spacer via a metal to metal joint between the first sealplate and the metallized tie layer.

2. The surgical instrument of claim 1, wherein the first nonmetallic sealplate spacer is attached to an external surface of the first sealplate.

3. The surgical instrument of claim 2, wherein the metallized tie layer is a first metallized tie layer, wherein the first jaw further comprises a second metallized tie layer between the first nonmetallic sealplate spacer and the first structural jaw element.

4. The surgical instrument of claim 2, wherein the first nonmetallic sealplate spacer is one of a group consisting of:
    a polymeric component;
    a ceramic component;
    a ceramic-polymer composite component;
    an undoped silicon component;
    a glass component; and
    an alumina-filled epoxy component.

5. The surgical instrument of claim 2, wherein the nonmetallic sealplate spacer has a thickness in the range of 0.001 inches to 0.02 inches.

6. The surgical instrument of claim 1, wherein the second jaw further includes a metallized tie layer between the second sealplate and the second nonmetallic sealplate spacer.

7. The surgical instrument of claim 6, wherein the second sealplate is fixed to the second nonmetallic sealplate spacer via a metal to metal joint between the second sealplate and the metallized tie layer.

8. The surgical instrument of claim 6, wherein the second nonmetallic spacer is one of a group consisting of:
    a polymeric component;
    a ceramic component;

a glass component; and
a ceramic-polymer composite component; and
a resin plastic injection molded component.

9. The surgical instrument of claim 1,
wherein the metallized tie layer is a first metallized tie layer,
wherein the metal to metal joint is a first metal to metal joint,
wherein the second jaw further includes a second metallized tie layer between the second sealplate and the second structural jaw element,
wherein the second sealplate is fixed to the second structural jaw element via a second metal to metal joint between the second sealplate and the second metallized tie layer.

10. The surgical instrument of any of claim 1, wherein the first and second sealplates are configured to facilitate sealing tissue via one of a group consisting of:
electrothermal sealing; and
ultrasonic sealing.

11. A medical instrument comprising:
a structural metal element;
a second metal element;
a nonmetallic spacer separating and electrically insulating the structural metal element from the second metal element;
at least one metalized tie layer on the nonmetallic spacer;
a first metal to metal joint between the structural metal element and the at least one metalized tie layer of the nonmetallic spacer; and
a second metal to metal joint between the structural metal element and the at least one metalized tie layer of the nonmetallic spacer.

12. The medical instrument of claim 11,
wherein the medical instrument is a tissue sealing medical instrument,
wherein the structural metal element, the second metal element, and the nonmetallic spacer form a jaw element of the tissue sealing medical instrument.

13. The medical instrument of claim 11, further comprising:
a second nonmetallic spacer on an external surface of the second metal element;
a second metalized tie layer on the second nonmetallic spacer; and
a third metal to metal joint between the second metal element and the second metalized tie layer.

14. The surgical instrument of claim 13, wherein the second nonmetallic spacer is one of a group consisting of:
a polymeric component;
a ceramic component;
a ceramic-polymer composite component;
a glass component; and
an undoped silicon component; and
an alumina-filled epoxy component.

15. The medical instrument of claim 13,
wherein the medical instrument is a tissue sealing medical instrument,
wherein the second metal element is a sealplate, and
wherein the second nonmetallic spacer is a nonmetallic sealplate spacer is on an external surface of the sealplate.

16. A surgical instrument comprising:
a first jaw including a first structural jaw element, a first sealplate fixed to the first structural jaw element, and a nonmetallic sealplate spacer separating and electrically insulating an external surface of the first sealplate and the first structural jaw element; and
a second jaw including a second structural jaw element and a second sealplate fixed to the second structural jaw element,
wherein the second structural jaw element is moveably coupled to the first structural jaw element to facilitate pinching tissue between the first and second sealplates, and wherein the first and second sealplates are configured to facilitate sealing tissue pinched therebetween,
wherein the first jaw further includes a metallized tie layer between the first sealplate and the nonmetallic sealplate spacer, wherein the nonmetallic sealplate spacer is fixed to the first sealplate via a metal to metal joint between the first sealplate and the metallized tie layer.

17. The surgical instrument of claim 16, wherein the nonmetallic sealplate spacer is one of a group consisting of:
a polymeric component;
a ceramic component;
a ceramic-polymer composite component;
a glass component; and
an undoped silicon component; and
an alumina-filled epoxy component.

18. The surgical instrument of claim 16, wherein the nonmetallic sealplate spacer has a thickness in the range of 0.001 inches to 0.02 inches.

19. The surgical instrument of claim 16, wherein the first jaw further comprises a nonmetallic spacer between the first structural jaw element and the first sealplate.

20. The surgical instrument of claim 19, wherein the nonmetallic spacer is overmolded on the first structural jaw element.

21. The surgical instrument of claim 19, wherein metallized tie layer is a first metallized tie layer, the first jaw further comprising a second metallized tie layer between the first structural jaw element and the first sealplate.

22. The surgical instrument of claim 19, wherein the nonmetallic spacer is one of a group consisting of:
a polymeric component;
a ceramic component;
a ceramic-polymer composite component;
a glass component; and
a resin plastic injection molded component.

23. The surgical instrument of claim 16, wherein the first and second sealplates are configured to facilitate sealing tissue via one of a group consisting of:
electrothermal sealing; and
ultrasonic sealing.

* * * * *